United States Patent [19]

Höhener et al.

[11] Patent Number: 5,037,979
[45] Date of Patent: Aug. 6, 1991

[54] CATIONIC COMPOUNDS

[75] Inventors: Alfred Höhener, Magden; Kurt Burdeska, Basel, Basle; Gerhard Reinert, Allschwil, all of Switzerland

[73] Assignee: Ciba-Geigy Corporation, Ardsley, N.Y.

[21] Appl. No.: 381,438

[22] Filed: Jul. 18, 1989

[30] Foreign Application Priority Data

Jul. 21, 1988 [CH] Switzerland ............ 2794/88

[51] Int. Cl.$^5$ ............ C07D 251/24; C07D 403/12; C07D 413/12; C07D 401/12
[52] U.S. Cl. .................... 544/216; 544/113; 540/598
[58] Field of Search .............. 544/113, 216; 540/598

[56] References Cited

U.S. PATENT DOCUMENTS 3,261,868 7/1966 Moffett et al. ............ 260/570.7

FOREIGN PATENT DOCUMENTS 108592 11/1983 European Pat. Off. .
7014151 5/1970 Japan .
405334 7/1966 Switzerland .
1011575 12/1965 United Kingdom .

OTHER PUBLICATIONS

W. Ley Chemie Faser Staffe, Schiele & Schön, Berlin (1978), pp. 132–141.
Chem. Abstract, vol. 73 (1970), 78488s, Tanaka et al.
M. F. Suettone et al., Int. J. Cosmetic Sci., 10, 99–109 (1988).

Primary Examiner—John M. Ford
Attorney, Agent, or Firm—George R. Dohmann; Edward McC. Roberts

[57] ABSTRACT

Novel cationic compounds of formula

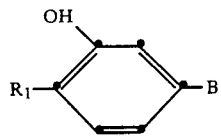

wherein $R_1$ and B are as defined in claim 1, are used for photochemically stabilizing basic dyeable polyamide, polyacrylonitrile and polyester fibre materials. The preparation of the novel compounds and of the novel starting materials is also described.

7 Claims, No Drawings

CATIONIC COMPOUNDS

The present invention relates to novel cationic compounds, to their preparation and to the use thereof for the photochemical stabilisation of basic dyeable polyamide, polyacrylonitrile and polyester fibre materials, as well as to the novel starting materials necessary for the preparation of the final products.

A substantial problem with differential dyeing carpets is the poor lightfastness of the basic dyeable polyamide component, especially the greening of the red component. It has now been found that this problem can be largely solved by dyeing the fibre materials with dye liquors which additionally contain novel cationic compounds.

Accordingly, the present invention relates to novel cationic compounds of formula

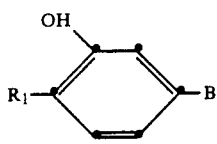  (1)

wherein B is a group of formula

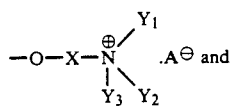  (Ia)

$R_1$ is a radical of formula

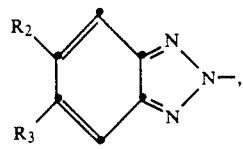

(2)

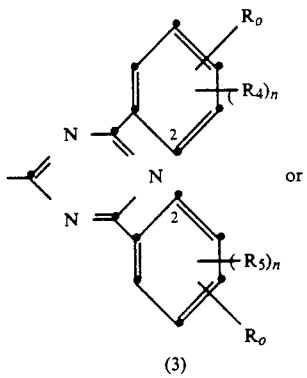

(3)

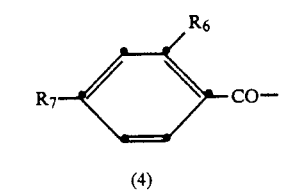

(4)

wherein
$R_0$ is hydrogen or hydroxy,
$R_2$ is hydrogen, halogen, $C_1$–$C_4$alkyl, $C_1$–$C_4$alkoxy, $C_2$–$C_9$alkoxycarbonyl or carboxy,
$R_3$ is hydrogen or halogen,
$R_4$ und $R_5$ are each independently of the other hydrogen, $C_1$–$C_4$alkyl,
$C_1$–$C_4$alkoxy or halogen or, if $R_0$ is hydroxy and n is 1, are also the group of formula (Ia),
$R_6$ is hydrogen, hydroxy or carboxy,
$R_7$ is hydrogen, hydroxy or $C_1$–$C_4$alkoxy,
n is 1 or 2,
X is $C_2$–$C_8$alkylene,
$Y_1$ is $C_1$–$C_4$alkyl or $C_1$–$C_4$alkyl which is substituted by halogen, cyano, hydroxy or $C_1$–$C_4$alkoxy or, when taken together with $Y_2$ and the linking nitrogen atoms, forms a 5- to 7-membered heterocyclic ring,
$Y_2$ is $C_1$–$C_4$alkyl or $C_1$–$C_4$alkyl which is substituted by halogen, cyano, hydroxy or $C_1$–$C_4$alkoxy or, when taken together with $Y_1$ and the linking nitrogen atom, forms a 5- to 7-membered heterocyclic ring,
$Y_3$ is hydrogen, $C_1$–$C_4$alkyl or $C_1$–$C_4$alkyl which is substituted by cyano, hydroxy, $C_1$–$C_4$alkoxy, phenyl or $C_1$–$C_4$alkoxycarbonyl, or is $C_3$–$C_4$alkenyl,
$Y_1$, $Y_2$ and $Y_3$, together with the linking nitrogen atom, are also the pyridino or picolino ring, and
$A^\ominus$ is a colourless anion.

Where n is 1 and $R_0$ is hydroxy, the hydroxy group is in 2-position and the group (Ia) is in 4-position. $R_0$ is preferably hydrogen.

A heterocyclic ring —$NY_1Y_2$ is typically a morpholino, piperidino, pyrrolidino or hexamethyleneimino ring (=hexahydro-1H-azepine).

$Y_1$, $Y_2$ and $Y_3$ are preferably unsubstituted $C_1$–$C_4$alkyl.

Particularly interesting compounds are those of formula

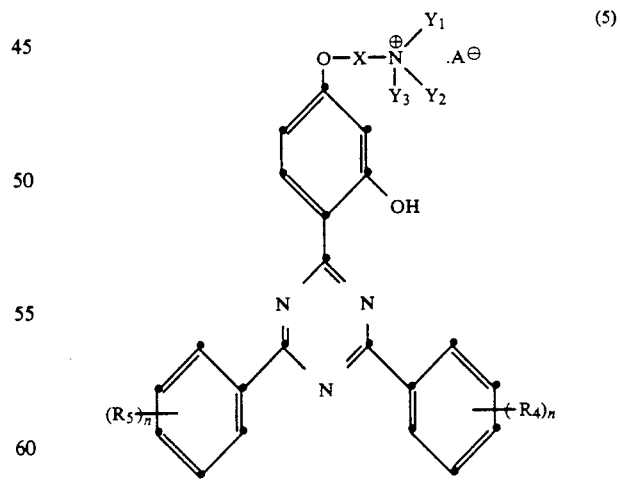  (5)

wherein
$R_4$ and $R_5$ are hydrogen or $C_1$–$C_4$alkyl,
X is $C_2$–$C_3$alkylene, and
$Y_1$, $Y_2$, $Y_3$, n and $A^\ominus$ are as defined for formula (1); and those of formula

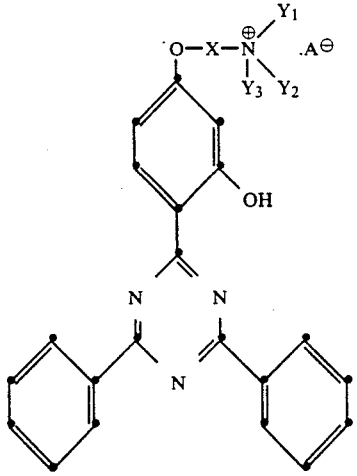

wherein
X is $C_2$-$C_3$alkylene,
$Y_1$ and $Y_2$ are unsubstituted $C_1$-$C_2$alkyl,
$Y_3$ is methyl or ethyl, and
$A^\ominus$ is $CH_3OSO_3^\ominus$ or $C_2H_5OSO_3^\ominus$.

In compounds of formula (5), $R_4$ and $R_5$ are preferably hydrogen or methyl.

Compounds of formula (1), wherein $R_1$ is the radical of formula (3), in which $R_0$ is hydroxy and n is 1, have the formula

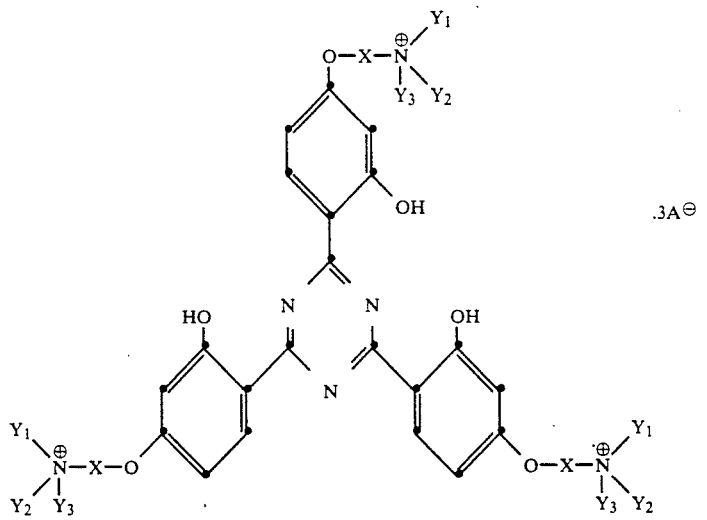

wherein X, $Y_1$, $Y_2$, $Y_3$ and $A^\ominus$ are as defined for formula (1).

Compounds of formulae (5) and (6) are prefered. Further interesting compounds are those
(a) of formula

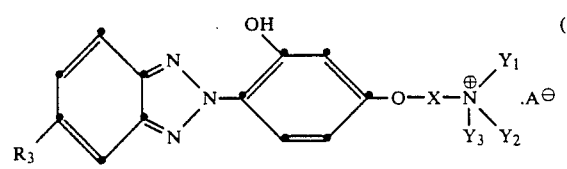

wherein
$R_3$ is hydrogen or chloro,
X is $C_2$-$C_3$alkylene, and
$Y_1$, $Y_2$, $Y_3$ and $A^\ominus$ are as defined for formula (1);
(b) of formula

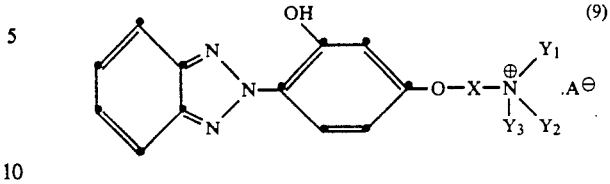

wherein
X is $C_2$-$C_3$alkylene,
$Y_1$ and $Y_2$ are unsubstituted $C_1$-$C_2$-alkyl,
$Y_3$ is methyl or ethyl, and
$A^\ominus$ is $CH_3OSO_3^\ominus$ or $C_2H_5OSO_3^\ominus$;
(c) of formula

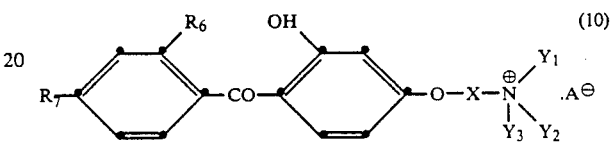

wherein X is $C_2$-$C_3$-alkylene and $R_6$, $R_7$, $Y_1$, $Y_2$, $Y_3$ and $A^\ominus$ are as defined for formula (1); and
(d) of formula

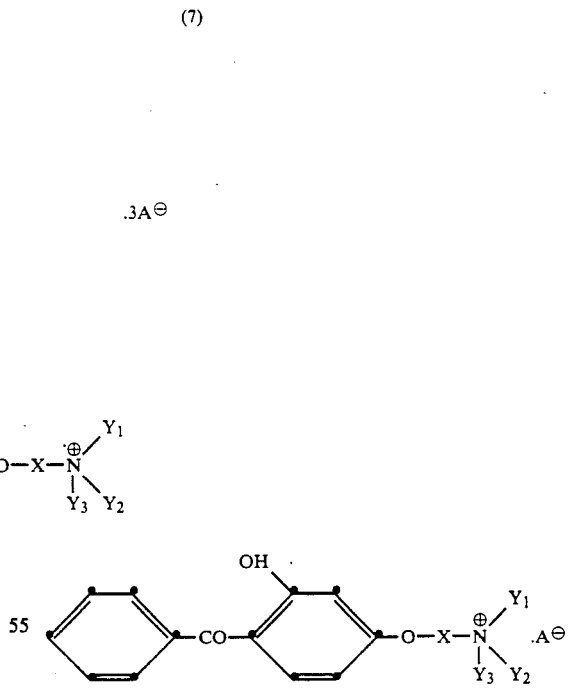

wherein
X is $C_2$-$C_3$-alkylene,
$Y_1$ and $Y_2$ are unsubstituted $C_1$-$C_2$-alkyl,
$Y_3$ is methyl or ethyl, and
$A^\ominus$ $CH_3OSO_3^\ominus$ or $C_2H_5OSO_3^\ominus$.

The substituents in the above formulae have the following meanings:
Halogen is fluoro, bromo and, preferably, chloro.
$C_1$-$C_4$Alkyl is methyl, ethyl, n-propyl, isopropyl, n-butyl, isobutyl, sec-butyl or tert-butyl.

$C_1$–$C_4$Alkoxy is methoxy, ethoxy, n-propoxy, isopropoxy, n-butoxy, iso-butoxy, sec-butoxy oder tert-butoxy.

$C_2$–$C_9$Alkoxycarbonyl is methoxycarbonyl, ethoxycarbonyl, n-propoxycarbonyl, n-butoxycarbonyl, pentoxycarbonyl, hexyloxycarbonyl, heptoxycarbonyl or octyloxycarbonyl.

The novel cationic compounds of formula (1) are prepared by quaternising or protonating 1 molar equivalent of a compound of formula

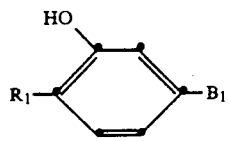  (12)

with 1 molar equivalent of an alkylating agent or of an acid of formula $Y_3$-A, at a temperature of from 0° to 180° C., in which formulae $B_1$ is the group of formula

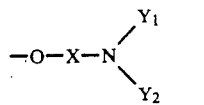  (Ib)

and $R_1$, $X_1$, $Y_1$, $Y_2$, and A are as defined for formula (1).

The quaternisation or protonation is conveniently carried out at a temperature of from 30° to 140° C.

Suitable quaternising or protonating agents $Y_3$-A are, for example: alkyl halides such as methyl iodide, ethyl iodide, ethyl bromide, butyl bromide or benzyl chloride; dialkyl sulfates such as dimethyl or diethyl sulfate; sulfonates such as methyl or ethyl toluenesulfonate or methyl or ethyl benzenesulfonate; alkylene oxides such as ethylene or propylene oxides or epichlorohydrin; acrylates such as methyl, ethyl or butyl acrylate, acrylonitrile; the compounds of formula

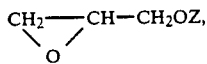

wherein Z is methyl, ethyl, propyl, butyl or phenyl; phosphites or phosphonates of formula

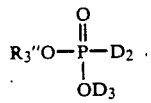

wherein $R_3''$ is $C_1$–$C_4$alkyl, $D_2$ is hydrogen, unsubstituted alkyl or alkyl which is substituted by hydroxy, cyano, alkylcarbonyloxy or alkoxycarbonyl, each containing 1 to 4 carbon atoms in the alkyl moiety, and $D_3$ is $C_1$–$C_4$alkyl.

The quaternisation of the compounds of formula (12) with alkyl halides, dialkyl sulfates or sulfonates to the compounds of formula (1) is conveniently carried out in a solvent which is inert to the alkylating agent. Examples of suitable solvents are hydrocarbons such as benzene, toluene and xylene; halogenated aliphatic or aromatic hydrocarbons such as chloroform, ethylene chloride, chlorobenzene and dichlorobenzene; alcohols such as ethanol, butanol, ethylene glycol and ethylene glycol monomethyl ether; ethers such as ethylene glycol dimethyl ether; and dioxane or amides such as dimethyl formamide and N-methylpyrrolidone.

The quaternisation with the cited alkylating agents is conveniently carried out at a temperature ranging from 0° to 180° C., preferably from 30° to 140° C.

The quaternisation of the compounds of formula (12) to the compounds of formula (1) with alkylene oxides, epichlorohydrin and derivatives thereof of formula

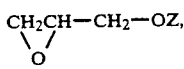

wherein Z has the meanings given above, acrylates or acrylonitrile, is carried out at the cited temperatures in acid medium, conveniently in the presence of an organic acid such as formic acid, acetic acid, propionic acid or benzoic acid. It is, however, also possible to use inorganic acids such as sulfuric acid, phosphoric acid or hydrohalic acids. These inorganic acids can be used in concentrated commercially available form, as dilute aqueous solutions or in admixture with the cited organic solvents, with or without the addition of water. When carrying out the reaction in the presence of an organic acid, the concentrated form of this acid will normally be used, if appropriate in admixture with the cited organic solvents.

Examples of preferred phosphites and phosphonates are dimethyl phosphite, diethyl phosphite, dimethyl methanephosphonate, diethyl methanephosphonate, methyl ethylmethanephosphonate, methyl propylmethanephosphonate, methyl butylmethanephosphonate, methyl hexylmethanephosphonate, methyl octylmethanephosphonate, methyl decylmethanephosphonate, methyl dodecylmethanephosphate, dimethyl β-hydroxyethanephosphonate, dimethyl β-acetoxyethanephosphonate, dimethyl β-methoxycarbonylethanephosphonate, and dimethyl β-cyanoethanephosphonate.

The reaction is carried out in water and/or an organic solvent such as methanol, ethanol, propanol, isopropanol, butanol, glycol, glycol methyl ether, glycol dimethyl ether, glycol butyl ether, diglycol methyl ether, methyl ethyl ketone, dimethyl formamide, sulfolane, oxypropionitrile, toluene, xylene, benzyl alcohol, phenoxyethanol, benzyloxypropionitrile, preferably at a temperature ranging from 60° to 190° C. When using liquid phosphites or phosphonates, it is also possible to carry out the reaction in the absence of an additional solvent.

If it is desired to obtain protonated compounds of formula (1), i.e. acid addition salts thereof, then preferably mineral acids are used as protonating agents. Suitable protonating agents are, in principle, all strong to medium strong organic acids or mineral acids.

Suitable solvents in which the protonation can be carried out are in general all inert solvents. Preferred solvents are those in which the starting material dissolves and from which the final product precipitates immediately. Such solvents are typically: aromatic hydrocarbons such as benzene, toluene and xylene; halogenated hydrocarbons such as trichloroethane, tetrachloroethylene, chlorobenzene or dichlorobenzene; and also nitro compounds such as nitromethane, nitropropane, nitrobenzene, alkanols and open-chain or cyclic ethers such as butanol, dibutyl ether, ethylene glycol, ethylene glycol monomethyl ether, ethylene glycol monoethyl ether, anisole or dioxane; ketones such as cyclohexanone or methyl ethyl ketone; fatty acid amides such as dimethylformamide or dimethylacetamide; sulfoxides such as dimethyl sulfoxide; and carboxylates such as ethyl acetate or butyl acetate.

The compounds of formula (12) are also novel and therefore constitute a further object of the present invention.

The compounds of formulae

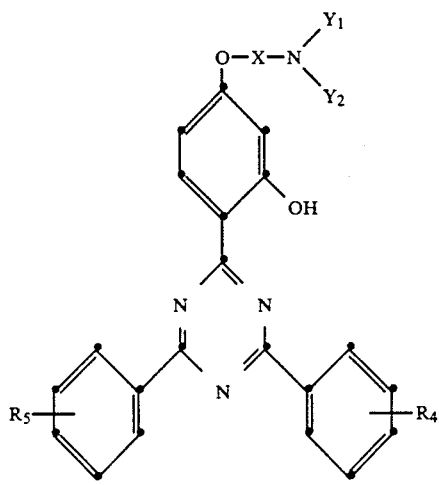 (13)

wherein
$R_4$ and $R_5$ are hydrogen, $C_1$–$C_4$alkyl, $C_1$–$C_4$alkoxy or halogen,
X is $C_2$–$C_3$alkylene, and
$Y_1$ and $Y_2$ are as defined for formula (1);

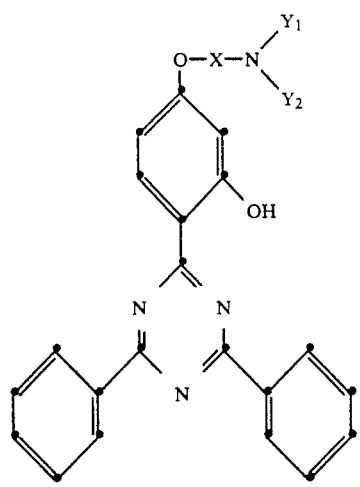 (14)

wherein X is $C_2$–$C_3$alkylene and $Y_1$ and $Y_2$ are unsubstituted $C_1$–$C_1$alkyl;

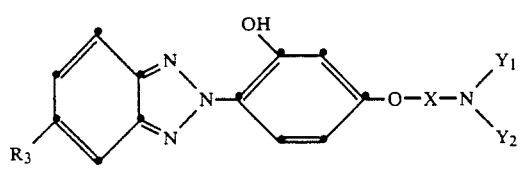 (15)

wherein
$R_3$ is hydrogen or chloro,
X is $C_2$–$C_3$alkylene, and
$Y_1$ and $Y_2$ are as defined for formula (1); and

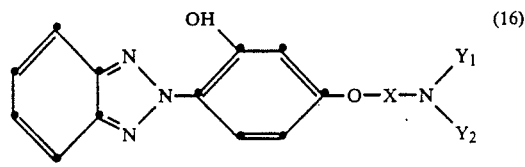 (16)

wherein X is $C_2$–$C_3$alkylene and $Y_1$ and $Y_2$ are unsubstituted $C_1$–$C_2$alkyl, constitute preferred embodiments of the compounds of formula (12).

The compounds of formula (12) can be prepared by reacting a compound of formula

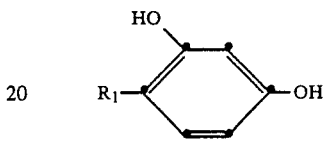

wherein $R_1$ is as defined above, which a compound of formula

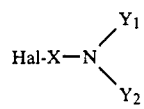

wherein Hal is chloro or bromo and X, $Y_1$ and $Y_2$ are as defined for formula (1), in the presence of a base, preferably sodium or potassium hydroxide.

The reaction is carried out at a temperature ranging from 60° to 120° C., preferably from 30° to 60° C.

The compounds of formula (12) can, however, also be prepared by reacting a compound of formula

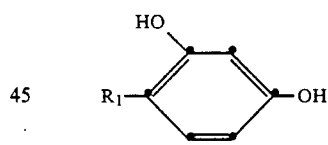

wherein $R_1$ is as defined above,
(a) with a compound of formula

Hal—X—OH wherein Hal is chloro or bromo and X is as defined above, in the presence of a base,
(b) reacting the resultant compound of formula

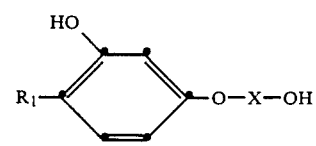

wherein $R_1$ and X are as defined above, with a halogenating agent, and
(c) reacting the resultant compound of formula

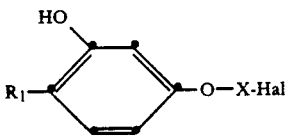

wherein $R_1$, X and Hal are as defined above, with a secondary or tertiary amine of formula

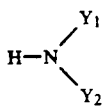

wherein $Y_1$ and $Y_2$ are defined for formula (1).

Examples of suitable halogenating agents are hydrohalic acids Hal-H, wherein Hal is chloro or bromo, thionyl chloride or thionyl bromide.

The first step (a) is carried out at a temperature ranging from 60° to 120° C., the second step (b) at a temperature ranging from 20° to 180° C., and the third step (c) at a temperature ranging from 100° to 200° C.

Accordingly, the present invention also relates to the processes for the preparation of compounds of formula (12).

The cationic light stabilisers of this invention are used for dyeing basic dyeable fibre materials, i.e. acid-modified polyamide and/or polyester fabrics, so as to stabilise the dyed fabrics against photochemical decomposition and to enhance the lightfastness of the dyeings.

The fibre materials which can be dyed in the presence of the novel light stabilisers are planar and are, in particular, floor coverings such as carpets. In addition to the above mentioned acid-modified fibre materials, they can consist of mixtures of unmodified (basic) polyamide and acid-modified polyamide and polyester materials. These materials are also known as differential dyeing polyamides and polyesters and are described, for example, in W. Loy, Chemiefaserstoffe, Schiele und Schön, Berlin 1978, pages 132–141.

The present invention thus also relates to a process for stabilising basic dyeable polyamide and polyester fibre materials. The process comprises treating said fibre materials with a dye liquor which, in addition to containing a disperse dye or cationic dye, further contains a compound of formula (1).

The cationic dyes suitable for the process of this invention may belong to different classes of dyes. They are in particular the customary salts, for example chlorides, sulfates or metal halides such as zinc chloride double salts of cationic dyes whose cationic character derives, for example, from a carbonium, oxonium, sulfonium or, preferably, ammonium group. Examples of such chromophoric systems are azo dyes, especially monoazo or hydrazone dyes, diphenylmethane dyes, triphenylmethane dyes, methine or azomethine dyes, coumarin, ketoimine, cyanine, azine, xanthene, oxazine or thiazine dyes. Finally, it is also possible to use dye salts of the anthraquinone series containing an external onium group, for example an alkylammonium or cycloammonium group, as well as benzo-1,2-pyran dye salts which contain the cycloammonium groups.

The eligible disperse dyes, which are only very slightly soluble in water and are substantially present in the dye liquor in the form of a fine dispersion, may belong to a very wide range of dyestuff classes, for example to the acridone, azo, anthraquinone, coumarin, methine, perinone, naphthoquinone, quinophthalone, styryl or nitro dyes.

Mixtures of cationic or disperse dyes may also be used in the process of this invention.

The present invention further relates to a process for stabilising mixtures of acid and basic dyeable polyamide fibre materials. This process comprises treating said fibre material with a liquor which, in addition to containing a cationic dye and a compound of formula (1), further contains an acid dye.

The acid dyes are typically salts of metal-free monoazo, disazo or polyazo dyes, including formazan dyes, as well as anthraquinone, xanthene, nitro, triphenylmethane and naphthoquinoneimine dyes. The acid character of these dyes is determined by acid salt-forming substituents such as carboxylic acid groups, sulfuric acid groups and phosphonate groups, phosphonic acid groups or sulfonic acid groups. These dyes may also contain in the molecule reactive groupings which form a covalent bond with the material to be dyed. Acid dyes which contain a single sulfonic acid group are preferred.

Mixtures of these acid dyes may also be used, for example mixtures of at least two or three acid dyes.

The present invention also relates to a process for stabilising acrylic fibres dyed with cationic dyes. This process comprises treating the fibre material with a liquor which, in addition to containing a migrating or non-migrating dye, further contains a compound of formula (1).

Suitable cationic dyes of this kind are those mentioned above.

The temperature at which dyeing is carried out is not less than 70° C. and normally will not exceed 106° C. The preferred temperature range is from 80° to 130° C.

The amount of dye used will depend on the desired depth of shade. In general, amounts of 0.001 to 10 percent by weight, preferably 0.01 to 5 percent by weight, have been sound suitable.

Suitable fibre material is synthetic acid-modified polyamide or acid-modified polyester, alone or also in blends. Synthetic acid-modified polyamide is typically that from adipic acid and hexamethylenediamine (polyamide 66), from ε-caprolactam (polyamide 6), from ω-aminoundecanoic acid (polyamide 11), from ω-aminoenanthic acid (polyamide 7), from ω-aminopelargic acid (polyamide 8), or from sebacic acid and hexamethylenediamine (polyamide 6, 10), which has been modified with carboxylic acids or sulfocarboxylic acids.

Acid-modified polyester is, for example, the polycondensate of terephthalic acid or isophthalic acid, ethylene glycol and sodium 3-(1,3- or 2,3-dihydroxypropoxy)propanesulfonate, sodium (2,3-dimethylolbutoxy)propanesulfonate, disodium isopropylidenedibenzoxypropylsulfonate or 3,5-dicarboxybenzenesulfonic acid, sulfonated terephthalic acid, sulfonated 4-methoxybenzenecarboxylic acid or sulfonated biphenyl-4,4'-dicarboxylic acid.

The liquors suitable for use in the process of this invention conveniently contain mineral acids, for example sulfuric acid or phosphoric acid; or organic acid such as formic acid, acetic acid, oxalic acid or, preferably, citric acid. They may also contain salts such as ammonium acetate, ammonium sulfate or sodium acetate. The acids are added in particular to adjust the pH of the formulations or liquors. The pH is normally in the range from 3 to 7, preferably from 3.5 to 4.5.

In addition to the light stabilisers, the dyes or fluorescent whitening agents, other assistants customarily used in dyeing may be used concurrently, for example dispersants, levelling agents, electrolytes, wetting agents, antifoams, foam inhibitors or thickeners.

The liquors may further contain photochemically active antioxidants such as copper complexes of bisazomethines. These copper complexes are disclosed, for example, in U.S. Pat. No. 4,655,783.

The invention is illustrated by the following Examples, in which parts and percentages are by weight.

EXAMPLE 1

20.5 g of 2-(2′,4′-dihydroxyphenyl)-4,6-diphenyl-1,3,5-triazine and 120 ml of cyclohexanol are heated to 60° C. Then 11.35 g of 2-diethylaminoethyl chloride hydrochloride and 7.4 g of 97% sodium methylate are added in succession. The mixture is heated to 120° C. and stirred for 2 hours at this temperature. The cyclohexanol is thereafter removed by vacuum distillation. The residue is stirred in 50 ml of ethanol, isolated by filtration, washed with ethanol and water and dried under vacuum at 60° C., affording 21 g of the product of formula

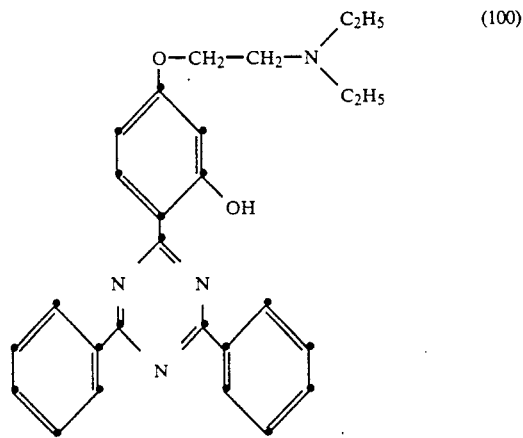
(100)

with a melting point of 94°–95° C.

The procedure described above is repeated, replacing 20.5 g of 2-(2′,4′-dihydroxyphenyl)-4,6-diphenyl-1,3,5-triazine by 22.4 g of 2-(2′,4′-dihydroxyphenyl)-4,6-bis(-2″,4″-dimethylphenyl)-1,3,5-triazine, to give the compound of formula

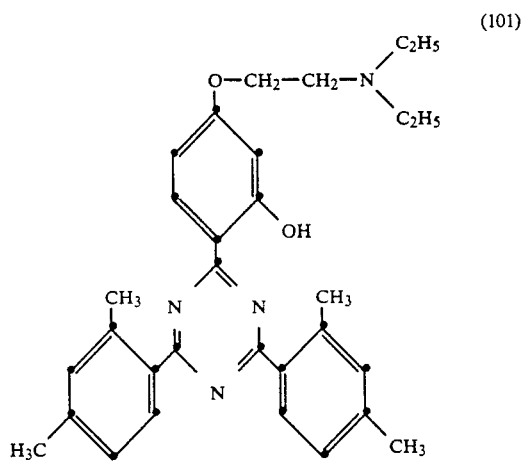
(101)

with a melting point of 112°–113° C.

The same procedure is repeated, replacing 11.35 g of 2-diethylaminoethyl chloride hydrochloride by 10.91 g of 3-dimethylamino-1-propyl chloride hydrochloride, to give the compound of formula

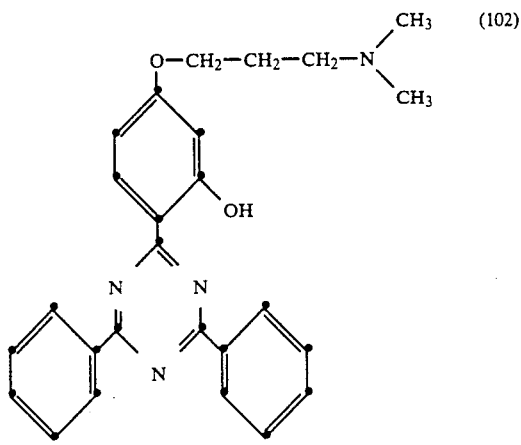
(102)

with a melting point of 124°–125° C.

Following the same procedure, the compounds

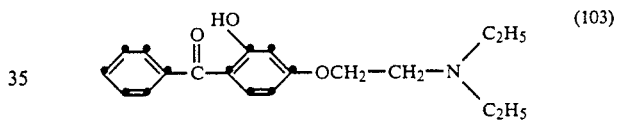
(103)

(in oily form) and

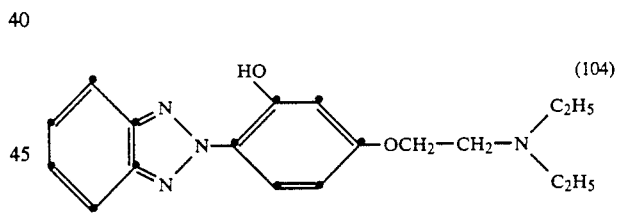
(104)

(in oily form) can be prepared from the 2,4-dihydroxybenzophenone and the 2,4-dihydroxyphenylbenztriazole.

EXAMPLE 2

13.2 g of the compound of formula (100), prepared according to Example 1, are dissolved in 100 ml of chlorobenzene. After addition of 4.16 g of dimethyl sulfate, the mixture is heated to 90° C. The densely precipitated product is stirred at 90° C. for 30 minutes, than cooled to 50° C., and filtered at room temperature after addition of 50 ml of acetone. The filter product is washed with acetone and dried, affording 16 g of a colourless product of formula

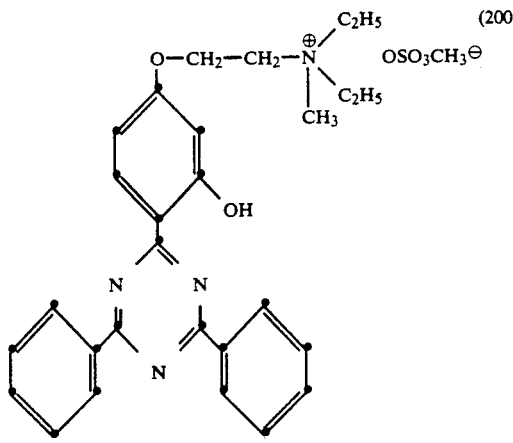

with a melting point of 221°-222° C.
The compound of formula

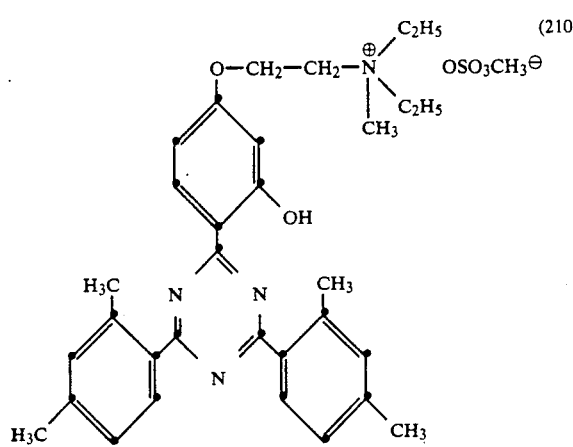

(m.p. 145°-146° C.) can be prepared in the same manner from 14.4 g of the compound of formula (101).

EXAMPLE 3

The procedure of Example 2 is repeated, replacing 13.2 g of the compound of formula (100) by 9.8 g of the compound of formula (103) or 8.9 g of the compound of formula (104), to give the compounds of formulae

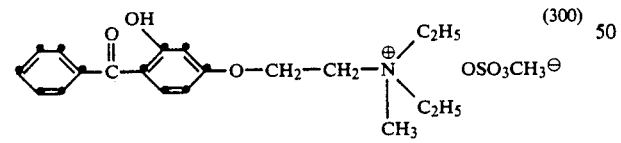

(in oily form) and

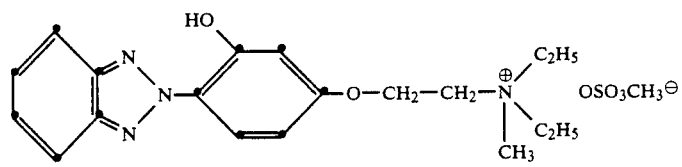

with a melting point of 126°-128° C.

EXAMPLE 4

The procedure of Example 2 is repeated, replacing 13.2 g of the compound of formula (100) by 12.8 g of the compound of formula (102), to give the compound of formula

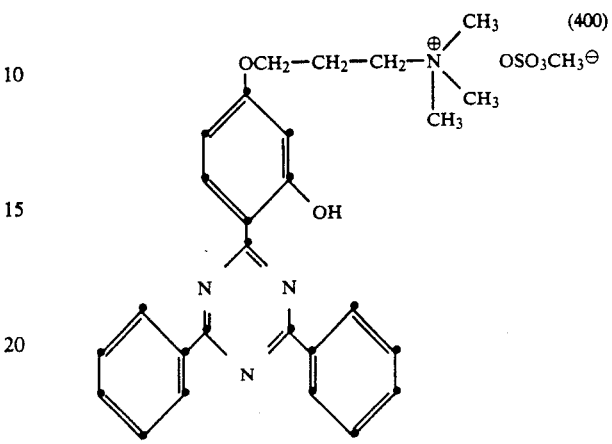

with a melting point of 291°-292° C.

EXAMPLE 5

27.3 g of 2-(2',4'-dihydroxyphenyl)-4,6-diphenyl-1,3,5-triazine in 275 ml of cyclohexanol are heated to 80° C. After addition of 4.96 g of sodium methylate, the mixture is heated to 100° C. and then 13.5 g of bromoethanol are added. The readily stirrable suspension is thereafter heated to 130°-135° C. and stirred at this temperature for 14 hours. The cyclohexanol is then removed by vacuum distillation and the residue is stirred in 50 ml of ethanol, isolated by filtration, washed with ethanol and water and dried under vacuum, affording 27.7 g of the product of formula

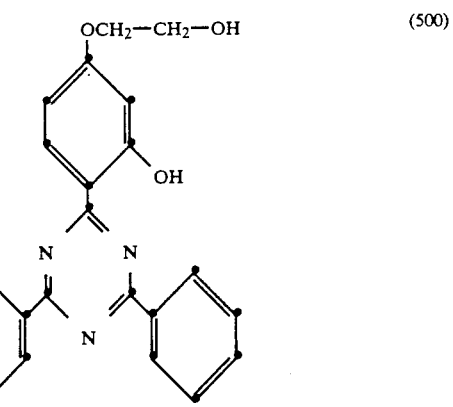

The compound crystallises from ethylene glycol monomethyl ether in the form of colourless crystals which melt at 230°-231° C.

EXAMPLE 6

46.3 g of the compound obtained in Example 5 are heated in 460 ml of chlorobenzene to 100° C. Then 15.7 g of thionyl chloride are added dropwise at 100°–110° C. over 1 hour, whereupon a clear solution forms. This solution is heated to 120° C. and stirred for 3 hour at this temperature. The chlorobenzene is then removed by vacuum distillation and the residue is treated with 50 ml of ethanol. The product is isolated by filtration, washed with ethanol and dried under vacuum at 80° C., affording 48.2 g of the compound of formula

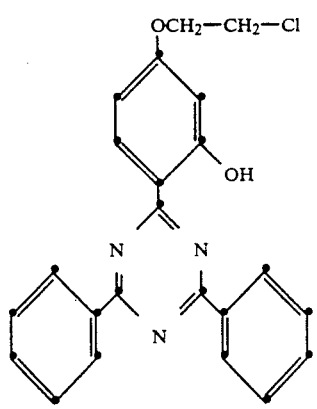
(600)

This compound crystallises from toluene in colourless crystals of m.p. 199°–200° C.

EXAMPLE 7

8.07 g of the compound described in Example 6 are heated to reflux in 25 ml of pyridine for 14 hours. The product which precipitates at boiling temperature is isolated by filtration at 20° C., washed with pyridine and acetone and dried, affording 8.9 g of the compound of formula

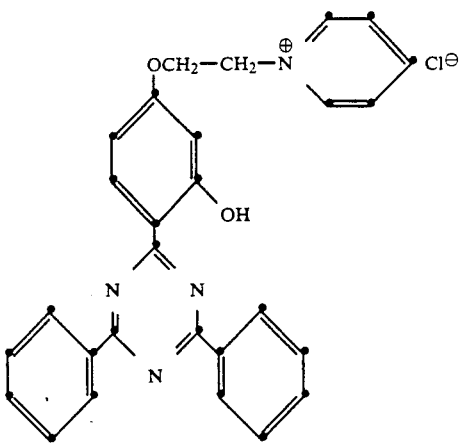
(700)

which melts at 244°–245° C.

EXAMPLE 8

Seven 10 g hanks of polyamide 66 staple yarn are treated in a dyeing machine (e.g. AHIBA ® dyeing machine) with liquors (liquor to goods ratio 1:50) which are adjusted with acetic acid to pH 4.5 and which contain the following dyes and ingredients (based on the fibre material):

the dye of formula

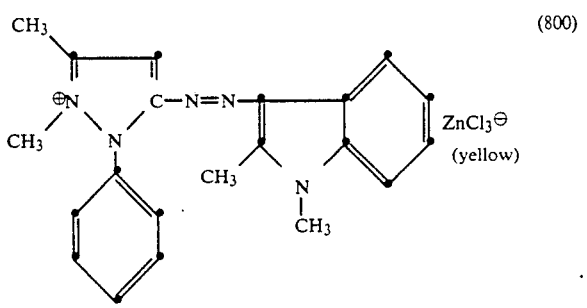
(800) (yellow)

the dye of formula

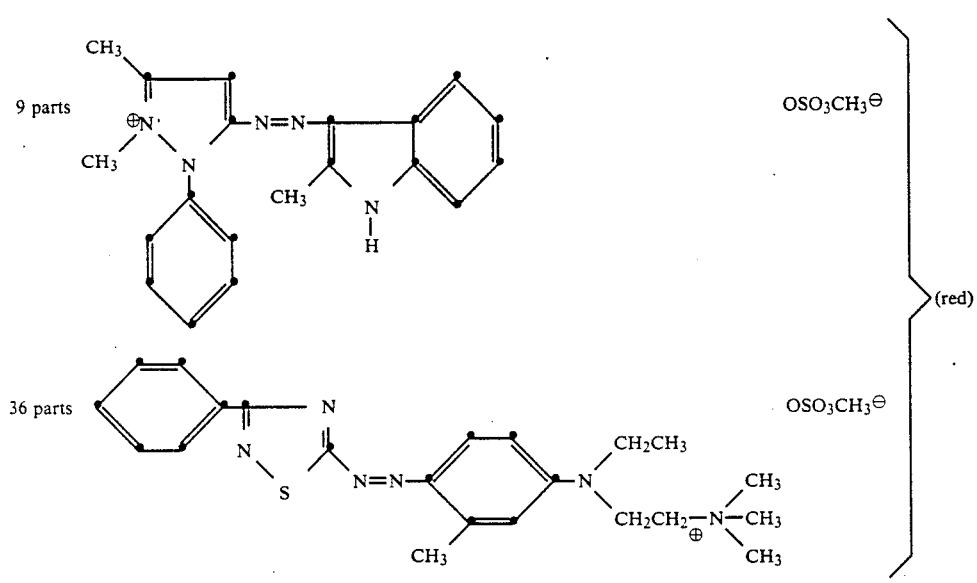
(801) (red)

the dye of formula

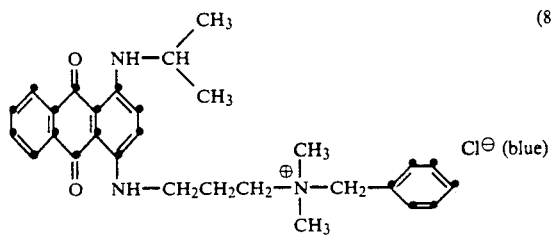

2% of a nonionic levelling agent

1st liquor: 0.06% of the dye of formula (800), 0.06% of the dye of formula (801), 0.02% of the dye of formula (802), 2nd liquor: as liquor 1 and additionally 0.2% of the compound of formula (200).

3rd liquor: as liquor 1 and additionally 0.5% of the compound of formula (200).

4th liquor: as liquor 1 and additionally 1.0% of the compound of formula (200).

5th liquor: as liquor 1 and additionally 0.05% of the compound of formula

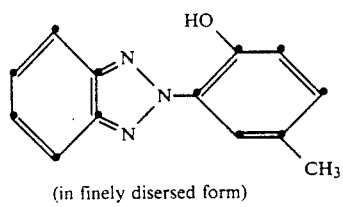

(in finely dispersed form)

6th liquor: as liquor 1 and additionally 0.2% of the compound of formula

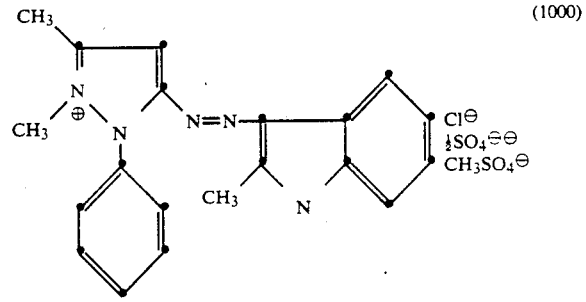

(in finely disersed form)

7th liquor: as liquor 1 and additionally 0.2% of the compound of formula (200) and 0.05% of the compound of formula (803) in finely dispersed form.

The material to be dyed is put into each liquor of 40° C. prepared as described above, treated for 5 minutes, and the liquor is heated to 95° C. at a rate of 1.5° C./min. Dyeing is carried out for 30 minutes at this temperature, then 1% of 80% acetic acid, diluted with water, is added, and dyeing is continued for a further 30 minutes. The liquor is then cooled and the dyeing is rinsed in cold water, centrifuged and dried at 80° C.

The dyeings are subsequently assessed for their lightfastness in accordance with the following methods:
fakra light in accordance with DIN 75 202, draft version (exposure to hot light) for 24 hours and 72 hours; xenon light in accordance with Swiss Standard SN-ISO 105-B02 for 300 and 500 hours.

The results are reported in Table 1.

TABLE I

| | Lightfastness | | | | Tensile strength/ |
| | fakra | | xenon | | elongation in % |
| Liquor | 24 h | 72 h | 300 h | 500 h | after 72 h fakra |
| --- | --- | --- | --- | --- | --- |
| 1 | <4 H | <4 H | 4–5 | 4–5 | decompose |
| 2 | 5 | 4 H | 5–6 | 5–6 | 10.7/14.4 |
| 3 | 6 | 4 H | 6+ | 6+ | 28.7/25.0 |
| 4 | 6 | 5 H | 6 | 6 | 49.9/42.1 |
| 5 | 5 G | 4 HG | 4 G | 4–5 G* | 86.6/79.3 |
| 6 | 6 | 4–5 H | 6 | 6 | 22.8/27.2 |
| 7 | 6–7 | 6 + H | 5 G | 5–6 | 99.0/88.1 |

EXAMPLE 9

Two 10 g hanks of polyamide 66 staple yarn are treated in a dyeing machine (e.g. AHIBA® dyeing machine) with liquors (liquor to goods ratio 1:50) which are adjusted to pH 4.5 with acetic acid and which contain the following ingredients (based on the fibre material):

1st liquor: 2.0% of a nonionic levelling agent,

2nd liquor: 2.0% of a nonionic levelling agent and 0.2% of the compound of formula (200).

The samples are then treated as described in Example 8 and assessed for their photochemical stability. The results are reported in Table II.

TABLE II

| | Stability | | | |
| | fakra | | xenon | |
| Liquor | 24 h | 72 h | 300 h | 500 h |
| --- | --- | --- | --- | --- |
| 1 | $A^x$ | $B^{xx}$ | | no visually perceptible difference |
| 2 | $A^x$ | $C^{xxx}$ | | |

$^x$A perceptible yellowing, but fibre intact
$^{xx}$B fibre yellowed and stability so impaired that fibre breaks when subjected to the slightest mechanical stress
$^{xxx}$C fibre very slightly yellowed

EXAMPLE 10

Three 10 g samples of a Dacron® 64 staple fabric (150 g/m$^2$) are each put into a dyeing machine for pressure bombs at a liquor to goods ratio of 1:20, each liquor containing 1 g/l of a levelling agent, 6 g/l of calcined Glauber's salt, 2% of 80% acetic acid and 0.05% of the yellow dye of formula liquor 1: contains no further ingredients.

liquor 2: additionally contains 0.5% of the compound of formula (400).

liquor 3: additionally contains 0.5% of the compound of formula (300).

(all percentages are based on the weight of the fabric).

The fabric is put at 50° C. into the prepared liquor, which is heated to 120° C. over 30 minutes. This temperature is kept for 60 minutes. The liquor is then cooled to 50° C. and the goods are rinsed with cold water and dried at 80° C. in a circulating air drier.

The lightfastness of the dyeings is assessed by exposure to xenon light (in accordance with Swiss Standard SN-ISO 105-BO2; evaluation according to the blue scale 1-8) and to fakra light (fastness to hot light) in accordance with DIN 75 202, evaluation according to the grey scale 1-5). The results are reported in Table III.

TABLE III

| | Lightfastness after | | |
|---|---|---|---|
| Liquor | xenon | fakra 72 h | fakra 144 h |
| 1 | 7-8 | 4+ | 3-4 H |
| 2 | 7-8 | 5 | 4-5 |
| 3 | 7-8 | 4-5 | 4 |

EXAMPLE 11

The procedure as described in Example 10 is repeated, using 0.06% of the red dye of formula

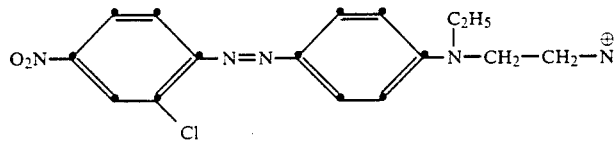

(1100)

liquor 1: contains no further ingredients.
liquor 2: contains 0.5% of the compound of formula (200).
liquor 3: contains 0.5% of the compound of formula (400).

The results are reported in Table IV.

TABLE IV

| | Lightfastness after | | |
|---|---|---|---|
| Liquor | xenon | fakra 72 h | fakra 144 h |
| 1 | 4-5 | 2-3 H | 2 H |
| 2 | 6-7 | 4 | −3-4 H |
| 3 | 6 | 3-4 H | 3 H |

EXAMPLE 12

The procedure of Example 11 is repeated, using 0.05% of the dye of formula

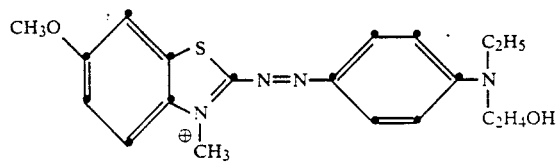

liquor 1: contains no further ingredients.
liquor 2: contains 0.5% of the compound of formula (400).
liquor 3: contains 0.5% of the compound of formula (200).
liquor 4: contains 0.5% of the compound of formula (300).
liquor 5: contains 0.5% of the compound of formula (201).

The results are reported in Table V.

TABLE V

| | Lightfastness* after | | |
|---|---|---|---|
| Liquor | xenon | fakra 72 h | fakra 144 h |
| 1 | 5 | 2 H | 1-2 H |
| 2 | 6+ | 3 H | −2-3 H |
| 3 | 6 | 2-3 H | 2 H |
| 4 | 5-6 | 2-3 H | 2 RH |
| 5 | 6 | 3 | −2-3 H |

*xenon according to the blue scale 1-8
fakra according to the grey scale 1-5

We claim:
1. A cationic compound of formula

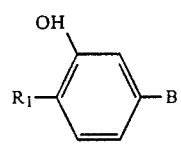 (1)

wherein B is a group of formula

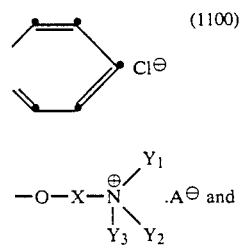

(Ia)

(1200)

$Cl^\ominus$/
$CH_3SO_4^\ominus$ $R_1$ is a radical of formula

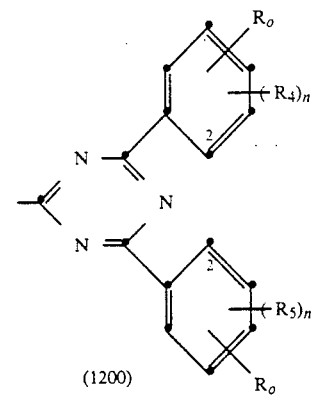 (3)

wherein
$R_0$ is hydrogen or hydroxy,
$R_4$ and $R_5$ are each independently of the other hydrogen, $C_1$-$C_4$alkyl, $C_1$-$C_4$alkoxy or halogen or, if $R_0$ is hydroxy and n is 1, are also the group of formula (Ia), n is 1 or 2,
X is $C_2$–$C_8$alkylene,
$Y_1$ is $C_1$–$C_4$alkyl or $C_1$–$C_4$alkyl which is substituted by halogen, cyano, hydroxy or $C_1$–$C_4$alkoxy or, when taken together with $Y_2$ and the linking nitrogen atom, forms a 5- to 7-membered heterocyclic ring selected from the group consisting of morpholino, piperidino, pyrrolidono and hexahydro-1H-azepine,
$Y_2$ is $C_1$–$C_4$alkyl or $C_1$–$C_4$alkyl which is substituted by halogen, cyano, hydroxy, or $C_1$–$C_4$alkoxy or, when taken together with $Y_1$ and the linking nitrogen atom, forms the 5- to 7-membered heterocyclic ring,
$Y_3$ is hydrogen, $C_1$–$C_4$alkyl or $C_1$–$C_4$alkyl which is substituted by cyano, hydroxy, $C_1$–$C_4$alkoxy, phenyl or $C_1$–$C_4$alkoxycarbonyl, or is $C_3$–$C_4$alkenyl,
$Y_1$, $Y_2$ and $Y_3$, together with the linking nitrogen atom, are also the pyridino or picolino ring, and
$A^\ominus$ is a colourless anion.

2. A compound according to claim 1, of formula (5)

3. A compound according to claim 2, of formula

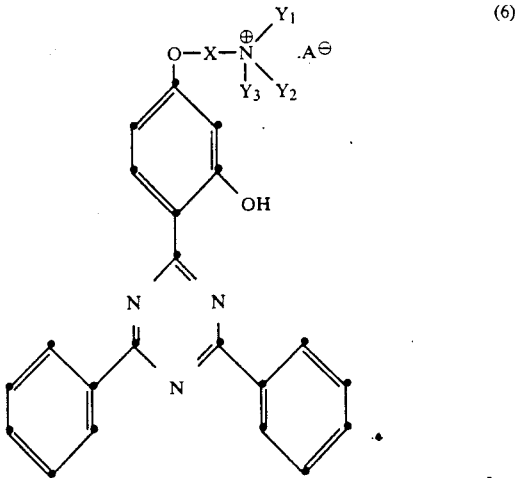

(6)

wherein
X is $C_2$–$C_3$alkylene,
$Y_1$ and $Y_2$ are unsubstituted $C_1$–$C_2$alkyl,
$Y_3$ is methyl or ethyl, and
$A^\ominus$ is $CH_3OSO_3^\ominus$ or $C_2H_5OSO_3^\ominus$.

4. A compound according to claim 1 of formula

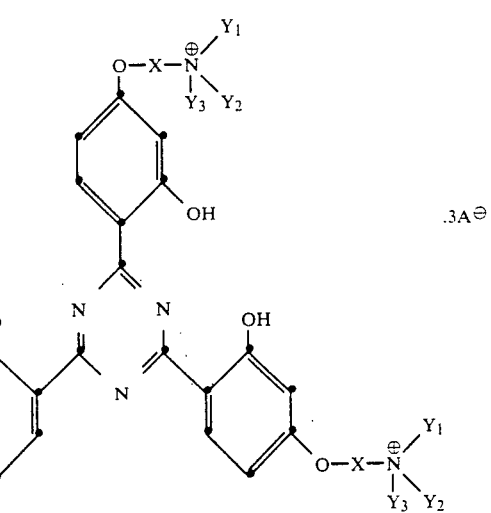

(7)

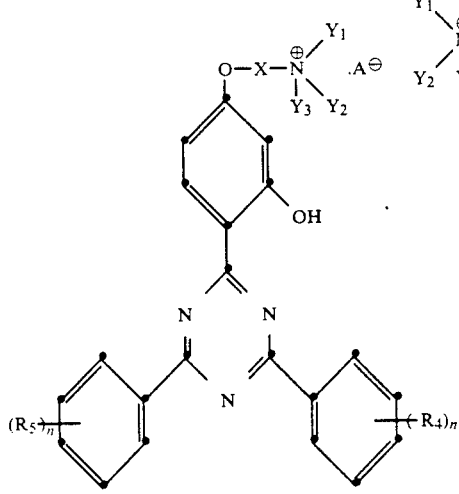

wherein
$R_4$ and $R_5$ are hydrogen or $C_1$–$C_4$alkyl,
X is $C_2$–$C_3$alkylene, and
$Y_1$, $Y_2$, $Y_3$, n and $A^\ominus$ are as defined in claim 1.

wherein X, $Y_1$, $Y_2$, $Y_3$ and $A^\ominus$ are as defined in claim 1.

5. A compound of formula

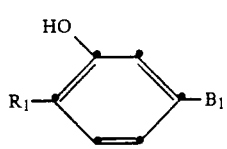

(12)

wherein $B_1$ is the group of formula

(Ib)

$R_1$ is a radical of formula

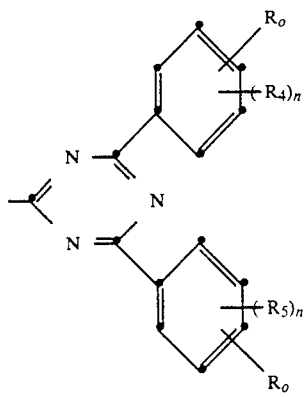

(3)

wherein

R₀ is hydrogen or hydroxy,

R₄ and R₅ are each independently of the other hydrogen, $C_1$-$C_4$alkyl, $C_1$-$C_4$alkoxy or halogen or, if R₀ is hydroxy and n is 1, are also the group of formula (Ib), n is 1 or 2, X is $C_2$-$C_8$alkylene, Y₁ is $C_1$-$C_4$alkyl or $C_1$-$C_4$alkyl which is substituted by halogen, cyano, hydroxy or $C_1$-$C_4$alkoxy, or, when taken together with Y₂ and the linking nitrogen atom forms a 5- to 7-membered heterocyclic ring selected from the group consisting of morpholino, pyrrolidino, piperidino and hexahydro-1H-azepine, and Y₂ is $C_1$-$C_4$alkyl or $C_1$-$C_4$alkyl which is substituted by halogen, cyano, hydroxy or $C_1$-$C_4$alkoxy, or, when taken together with Y₂ and the linking nitrogen atom forms the 5- or 7-membered heterocyclic ring.

6. A compound according to claim 5 of formula

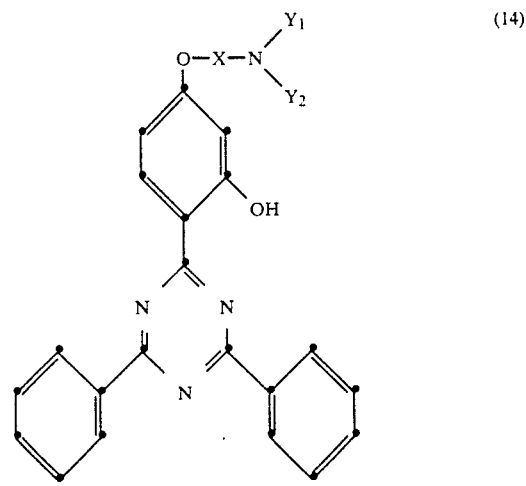

(13)

wherein

R₄ and R₅ are hydrogen or $C_1$-$C_4$alkyl,

X is $C_2$-$C_3$alkylene, and

Y₁ and Y₂ are as defined in claim 5.

7. A compound according to claim 6 of formula (14)

wherein X is $C_2$-$C_3$alkylene and Y₁ and Y₂ are unsubstituted $C_1$-$C_2$alkyl.

* * * * *